United States Patent [19]
Sakuta et al.

[11] Patent Number: 5,270,426
[45] Date of Patent: Dec. 14, 1993

[54] ORGANOSILICON COMPOUND

[75] Inventors: Koji Sakuta; Satoshi Kuwata, both of Gunma, Japan

[73] Assignee: Shin-Etsu Chemical Co., Ltd., Tokyo, Japan

[21] Appl. No.: 987,081

[22] Filed: Dec. 7, 1992

Related U.S. Application Data

[63] Continuation of Ser. No. 643,619, Jan. 22, 1991, abandoned.

[30] Foreign Application Priority Data

Jan. 22, 1990 [JP] Japan ................................. 2-12874

[51] Int. Cl.$^5$ .............................................. C08G 77/12
[52] U.S. Cl. ....................................... 528/15; 528/25; 556/436; 556/479
[58] Field of Search ..................... 525/15, 25; 556/436, 556/479

[56] References Cited

U.S. PATENT DOCUMENTS

| | | | |
|---|---|---|---|
| 4,391,963 | 7/1983 | Shirahata ............................... | 528/37 |
| 4,467,082 | 8/1984 | Shirahata et al. .................... | 556/436 |

FOREIGN PATENT DOCUMENTS

| | | |
|---|---|---|
| 96259 | 1/1989 | Japan . |
| 51542 | 2/1990 | Japan . |
| 187437 | 2/1990 | Japan . |

*Primary Examiner*—Melvyn I. Marquis
*Attorney, Agent, or Firm*—Millen, White, Zelano & Branigan

[57] ABSTRACT

This invention discloses a novel organosilicon compound, which is soluble in silicone oils and strongly absorbs ultraviolet light, represented by the general formula:

An organosilicon compound having a benzophenone skeleton represented by the general formula:

$$R^1{}_3SiO\text{--}(SiO)_n\text{--}Si\text{--}R^2$$

with $R^1$ groups on the silicons, where "n" is an integer in the range 0~100, $R^1$ are similar or dissimilar saturated hydrocarbon groups with a number of carbon atoms in the range 1-30 or phenyl group, $R^2$ is a monofunctional organic group represented by the formula $-(CR^3{}_2 CR^3(H) CR^3{}_2)-R^4$, $R^3$ is hydrogen atom or a saturated monofunctional hydrocarbon group with 1-5 carbon atoms, and $R^4$ is a group represented by the formula:

[benzophenone structure with $R^5$, OH, $(R^6O)_b$, $(OR^6)_a$ substituents] or [benzophenone structure with $R^5$, OH, $(R^6O)_b$, $(OR^6)_a$ substituents]

wherein $R^5$ is a hydrogen atom or hydroxyl group, $R^6$ are hydrogen atoms, or similar or dissimilar monofunctional saturated or unsaturated hydrocarbon groups with 1-10 carbon atoms, "a" is an integer in the range 0-3, and "b" is an integer in the range 0-4.

2 Claims, 4 Drawing Sheets

ORGANOSILICON COMPOUND

This application is a continuation of application Ser. No. 07/643,619, filed Jan. 22, 1991 and now abandoned.

FIELD OF THE INVENTION

This invention concerns an organosilicon compound and, in particular, a novel organosilicon compound which is soluble in silicone oils and strongly absorbs ultraviolet light.

BACKGROUND OF THE INVENTION

Ultraviolet absorbents with a benzophenone skeleton have conventionally been used as compounding agents in the medical and cosmetic fields, or as additives for various plastics. As, however, the dispersivity and solubility of these absorbents in substrates were poor, there was a limit to their blending proportion, and bleeding also occurred due to the low stability of the dispersions. Further, although silicone oils are used in many different fields, benzophenone compounds were particularly difficult to dissolve in silicone oils.

To overcome these disadvantages, benzophenone skeletons have been introduced into polysiloxane molecules by converting compounds having such a skeleton to alkyl ether derivatives with hydrolyzable groups such as alkoxysilyl, making use of the phenolic hydroxyl group, and hydrolyzing them together with chlorosilanes or alkoxysilanes (Japanese Patent Kokai (Unexamined Published Japanese Patents) 21432/'82, 10591/'83, 213075/'83, 11130/'86 and 187740/'87).

Benzophenone skeletons have been introduced into polysiloxane molecules also by reacting isocyanates with hydrolysable groups such as alkoxysilyl together with the phenolic hydroxyl groups of compounds having such a skeleton so as to obtain carbamoyloxy derivatives, and then hydrolyzing them together with chlorosilanes or alkoxysilanes (Japanese Patent Kokai 21390/'82).

In both of these methods, however, as the derivatives with a benzophenone skeleton have an alkoxysilyl group, they also tend to be hydrolyzed when used in admixture with polysiloxanes which have no reactive functional groups, and their stability is poor. In particular, when these compounds with hydrolyzable groups are used in medical or cosmetic preparations, there is a further problem in that the substances produced by hydrolysis cause irritation to the skin and mucous membranes.

Although the use of silicone oils in medical and cosmetic preparations has been increasing in recent years, a compound with a benzophenone skeleton which not only was very soluble in silicone oils, but which also did not have hydrolyzable groups and was therefore stable, had not yet been obtained.

The inventors of the present invention, after various experiments, discovered that by introducing non-reactive organosilicon or organopolysiloxane groups into the benzophenone skeleton, the product obtained had excellent solubility in substrates and especially silicone oils, and thereby arrived at the present invention.

SUMMARY OF THE INVENTION

The object of the present invention is, therefore, to provide a novel ultraviolet absorbent characterized by having a benzophenone skeleton with the property of absorbing ultraviolet light, which has excellent solubility in substrates and especially in silicone oils.

The above object of this invention is attained by an organosilicon compound having a benzophenone skeleton represented by the general formula:

where "n" is an integer in the range 0–100, $R^1$ are similar or dissimilar saturated hydrocarbon groups with a number of carbon atoms in the range 1–30 or a phenyl group, $R^2$ is a monofunctional organic group represented by the formula $-(CR_2{}^3CR^3(H)CR_2{}^3)-R^4$, $R^3$ is a hydrogen atom or a saturated monofunctional hydrocarbon group with 1–5 carbon atoms, and $R^4$ is a group represented by the formula:

$R^5$ is a hydrogen atom or hydroxyl group, $R^6$ are hydrogen atoms, or similar or dissimilar monofunctional saturated or unsaturated hydrocarbon groups with 1–10 carbon atoms, "a" is an integer in the range 0–3, and "b" is an integer in the range 0–4.

The organosilicon compound of this invention not only has a high ultraviolet absorption factor but is also highly soluble in silicone oils, and, if added to silicone oils, it easily confers the property of ultraviolet absorption on them. Further, it does not possess alkoxysilyl or other reactive groups, and is, therefore stable. In addition, as it does not cause much skin irritation, it is particularly useful for application in cosmetic preparations.

DETAILED DESCRIPTION OF THE INVENTION

The novel organosilicon compound of this invention may be easily synthesized, after obtaining an allyl precursor via a rearrangement according to known methods, by carrying out a hydrosilylation reaction.

The benzophenone type ultraviolet absorbent starting material is represented by the general formula:

where "a" is an integer in the range 0-3, and "b" is an integer in the range 0-4. Typical compounds are:

2-hydroxybenzophenone

2,4-dihydroxybenzophenone

2-hydroxy-4-methoxybenzophenone

2-hydroxy-4-octoxybenzophenone 2,2'-dihydroxy-4,4'-dimethoxybenzophenone 2,2'-dihydroxy-4-methoxybenzophenone 2,2',4,4'-tetrahydroxybenzophenone.

These benzophenone type compounds, after allyl etherification of the phenol part under basic conditions, are converted to allyl derivatives or by a rearrangement brought about by the action of heat. To promote the rearrangement of the allyl ether, a necessary condition is that at least one position of ortho or para positions against the phenolic OH group(s) of the benzophenone compound starting material is unsubstituted.

The benzophenone derivative thus obtained is then made to undergo an addition reaction with an organohydrogen silane or polysiloxane represented by the general formula:

in the presence of a platinum, palladium or rhodium compound as catalyst so as to obtain the novel organosilicon compound of this invention represented by the general formula:

Examples of $R^1$ are saturated aliphatic hydrocarbon groups such as methyl, ethyl, propyl, butyl, pentyl, hexyl, heptyl, octyl, nonyl and decyl; saturated alicyclic hydrocarbon groups such as cyclopentyl and cyclohexyl; aromatic hydrocarbon groups such as phenyl and tolyl; and halogenated hydrocarbon groups such as trifluoropropyl, nonafluorohexyl, heptadecafluorodecyl, chloropropyl and chlorophenyl, but it is preferable that the proportion of methyl is no less than 50%.

The organosilicon compound of this invention obtained as described above has a benzophenone skeleton which absorbs ultraviolet light. It is, therefore, extremely useful for many different applications such as compounding agents for medical and cosmetic preparations, additives for polishes such as car wax, additives for various types of plastics and additives for plastic surface coatings.

EXAMPLES

We shall now explain this invention in more detail with reference to specific examples, but it should be understood that it is no way limited by them.

EXAMPLE 1

45.6 g of the reagent below:

(I)

and toluene (300 g) were introduced into a reaction vessel, and the mixture was stirred at room temperature for 30 minutes with the gradual addition of a 28 wt % solution of sodium methoxide in methanol (46.3 g) from a dropping funnel. The reaction vessel was heated to 100° C. on an oil bath while introducing nitrogen gas, the vessel was cooled to room temperature after removing 48 g of solvent, and allyl bromide (34.0 g) and dimethylformamide (100 g) were then added gradually from the dropping funnel.

After the addition was complete, the mixture was refluxed for 5 hours, and the salt produced was filtered and washed with water. The remaining solvent was removed under reduced pressure, the residue was heated at 240°-250° C. (under a reduced pressure 35 mm Hg) for 1 hour, and distilled to obtain the allyl derivative with the formula:

in a yield of 46.2 g.

The allyl derivative obtained was a yellow transparent liquid with a boiling point of 221°-225° C. (under a reduced pressure of 9 mm Hg), and a viscosity of 677 cs at 25° C. The above allyl derivative (43.0 g) was introduced together with toluene (100 g) and a 2 wt % 2-propanol solution of chloroplatinic acid (0.05 g) into a reaction vessel, and the reagent with the formula below, methyl hydrogen polysiloxane:

(II)

was added gradually (71.2 g) from a dropping funnel after raising the internal temperature to 80° C. When the addition was complete, the internal temperature was maintained at 80°-90° C. and the mixture was stirred for 8 hours.

After the reaction liquid was cooled to room temperature, active carbon (0.5 g) was added, and stirring was continued at room temperature for a further 2 hours. After filtering off the active carbon, the liquid was heated under reduced pressure (5 mm Hg) at 150° C. for 2 hours to remove solvent and unreacted methyl hydrogen polysiloxane and obtain the desired organosilicon compound:

The product, which was obtained in 98.0 g yield, was a yellow transparent liquid having a viscosity of 88.4 cs at 25° C.

Figure 1:
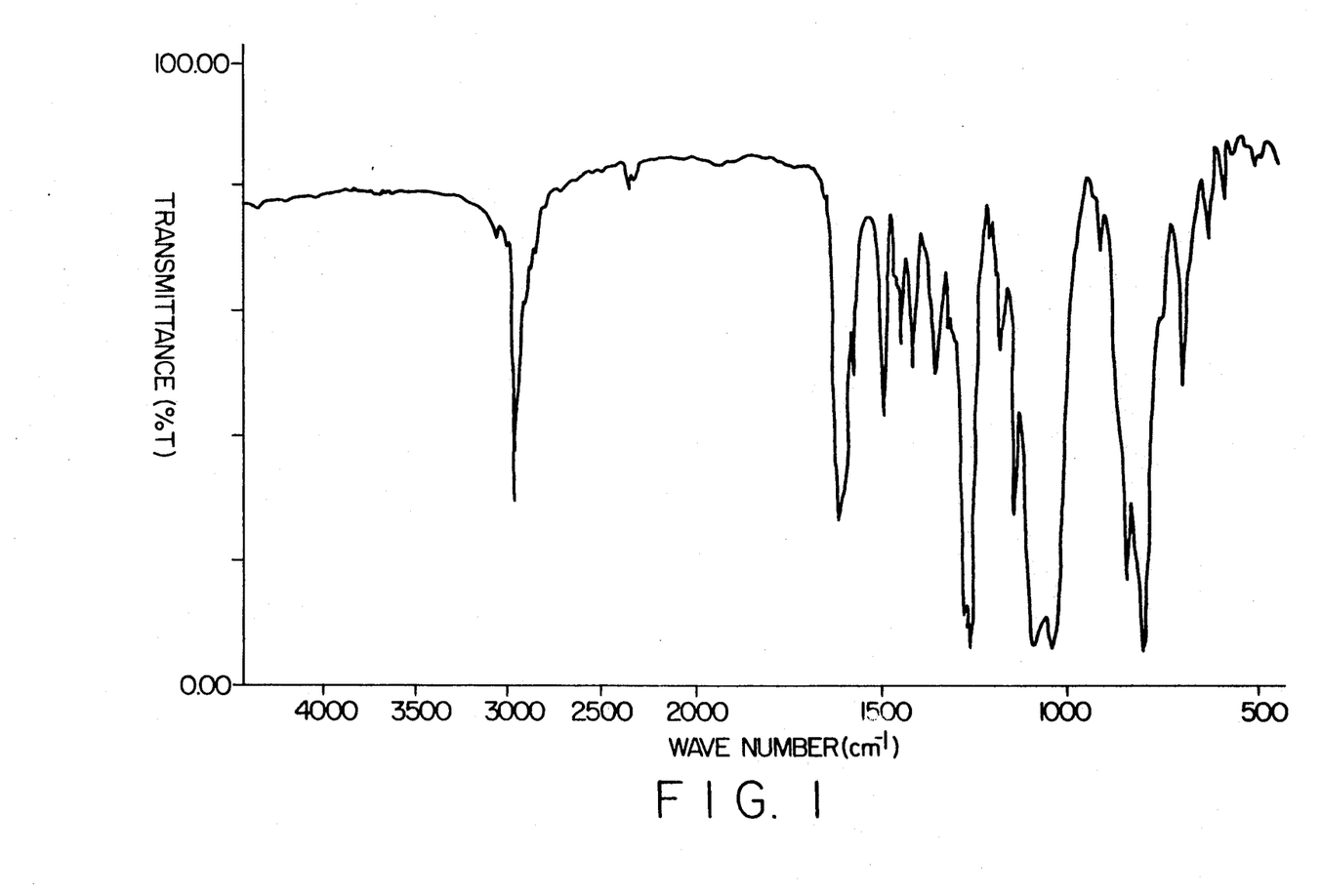
FIG. 1 shows the infrared absorption spectrum of the organosilicon compound of this invention obtained in Example 1.
Figure 2:
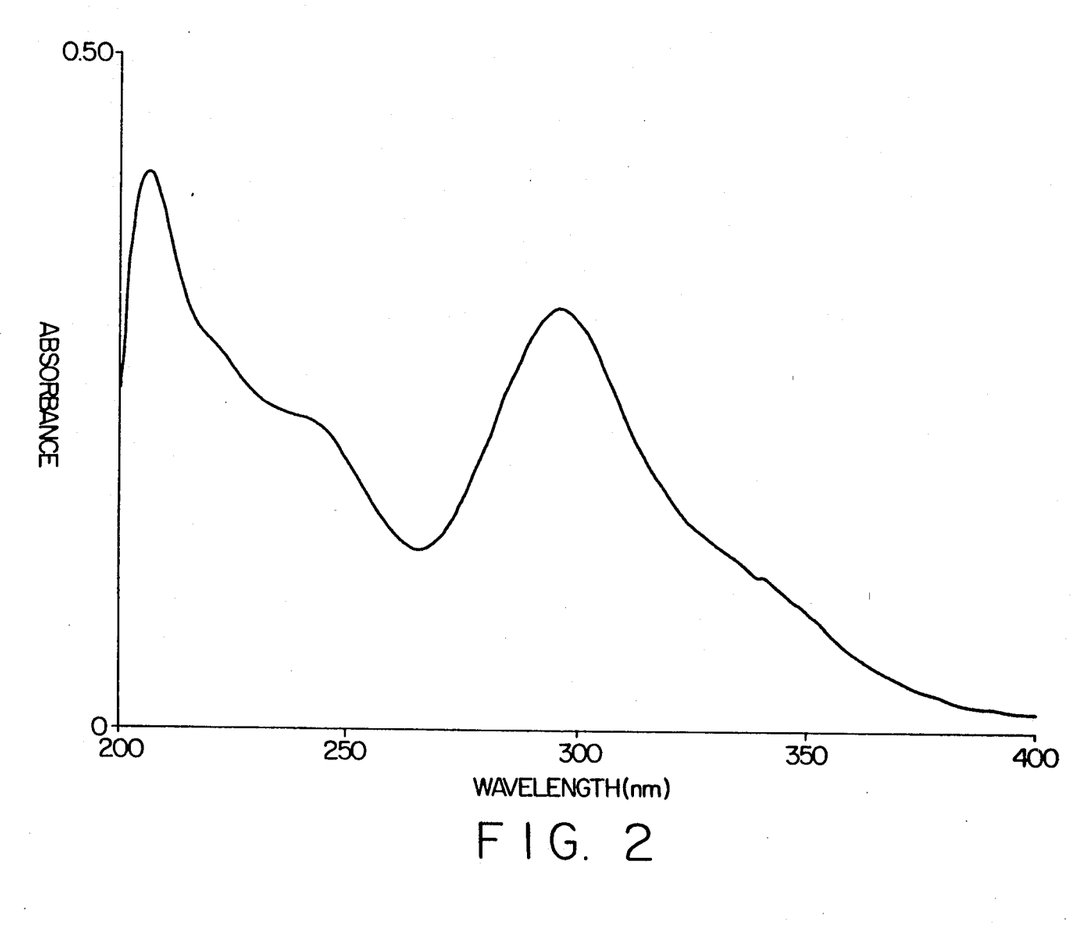
FIG. 2 shows the ultraviolet absorption spectrum of the organosilicon compound of this invention obtained in Example 1.

The infrared and ultraviolet spectra of the product are shown in FIG. 1 and FIG. 2 respectively.

The solute concentration of the sample used for measuring the ultraviolet spectrum was 1.09 mg/100 ml ethanol.

Further, the solubility of the organosilicon compound at room temperature when added to various silicone oils in a proportion of 10 wt %, is as shown in Table 1.

In table 1, *1) represents the following compound;

TABLE 1

| Silicone Oil | Organosilicon Compound of this Invention | |
|---|---|---|
| | Example 1 | Example 2 |
| Octamethylcyclotetrasiloxane | Homogeneous solution (transparent) | Homogeneous solution (transparent) |
| Dimethylpolysiloxane (viscosity 10 cs) | Homogeneous solution (transparent) | Homogeneous solution (transparent) |
| Dimethylpolysiloxane (viscosity 100 cs) | Homogeneous solution (transparent) | Homogeneous solution (transparent) |
| Dimethylpolysiloxane (viscosity 1000 cs) | Homogeneous solution (transparent) | Homogeneous solution (transparent) |
| Methylphenylpolysiloxane (5 mole % phenyl groups, viscosity 200 cs) | Homogeneous solution (transparent) | Homogeneous solution (transparent) |
| Methylphenylpolysiloxane (25 mole % phenyl groups, viscosity 400 cs) | Homogeneous solution (transparent) | Homogeneous solution (transparent) |
| Methylalkylpolysiloxane*1) (viscosity 100 cs) | Homogeneous solution (transparent) | Homogeneous solution (transparent) |
| Methyltrifluoropropylpolysiloxane (15 mole % trifluoropropyl groups, viscosity 36 cs) | Homogeneous solution (transparent) | Homogeneous solution (transparent) |

EXAMPLE 2

50.0 g of the reagent below:

(III)

were introduced into a reaction vessel together with calcium carbonate (32.2 g), allyl bromide (31.0 g) and acetone (200 g), and the mixture was refluxed for 6 hours.

The salt produced was filtered and concentrated, toluene (200 g) was added to the residue, and the mixture was washed with water. After again removing solvent under reduced pressure, the residue was heated at 240°–250° C. (under a reduced pressure of 10 mm Hg) for 2 hours, and distilled to obtain the allyl derivative with the formula:

in a yield of 52.0 g.

The allyl derivative obtained was a light yellow solid with a boiling point of 220°–230° C. (under a reduced pressure of 5 mm Hg), and a melting point of 158°–165° C.

The above allyl derivative (20.0 g), toluene (50.0 g), a 2 wt % 2-propanol solution of chloroplatinic acid (0.05 g) and the before mentioned reagent II (32.0 g) were then used to obtain the desired organosilicon compound as in Example I. The product, which was obtained in 43.0 g yield, was a viscosity of 624 cs at 25° C.

Figure 3:
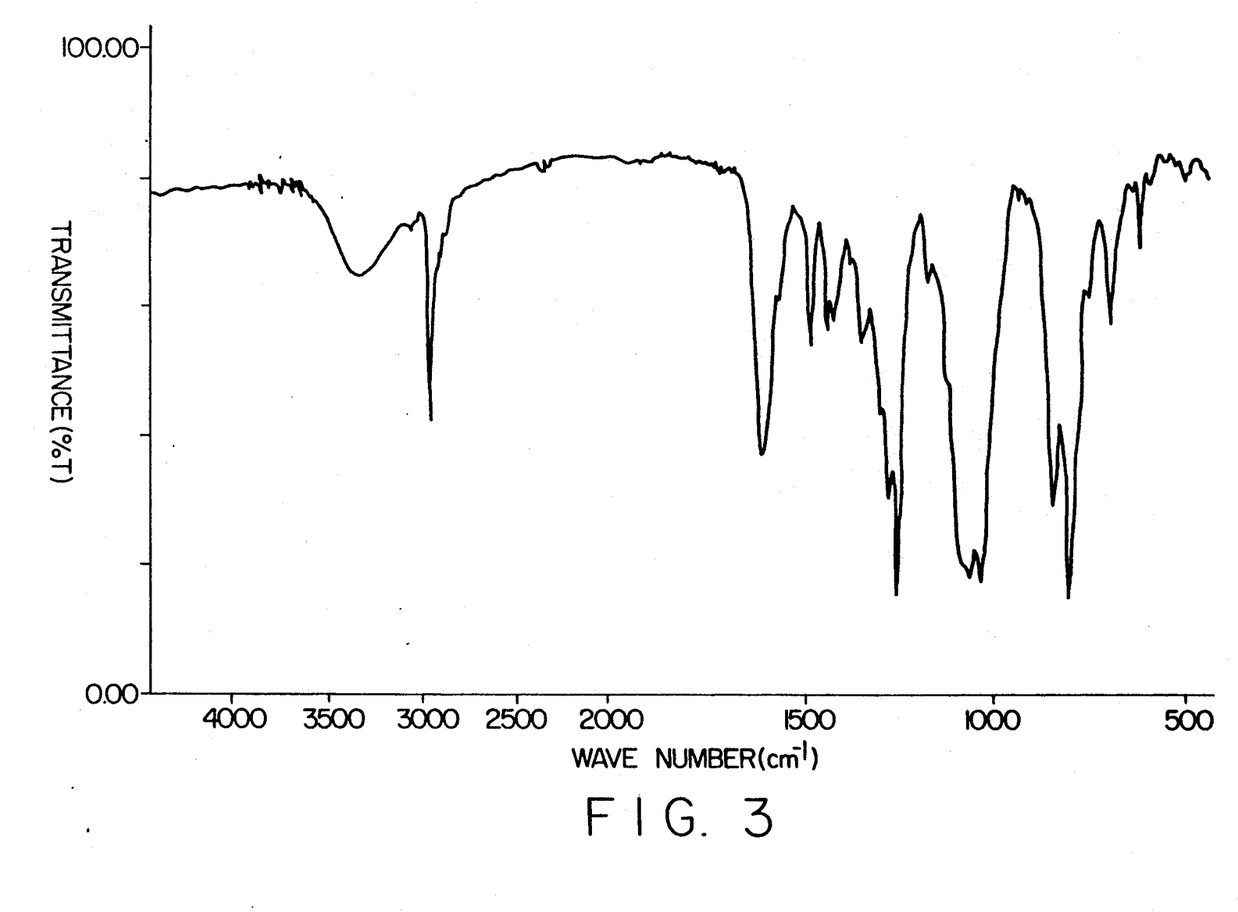
FIG. 3 shows the infrared absorption spectrum of the organosilicon compound of this invention obtained in Example 2.
Figure 4:
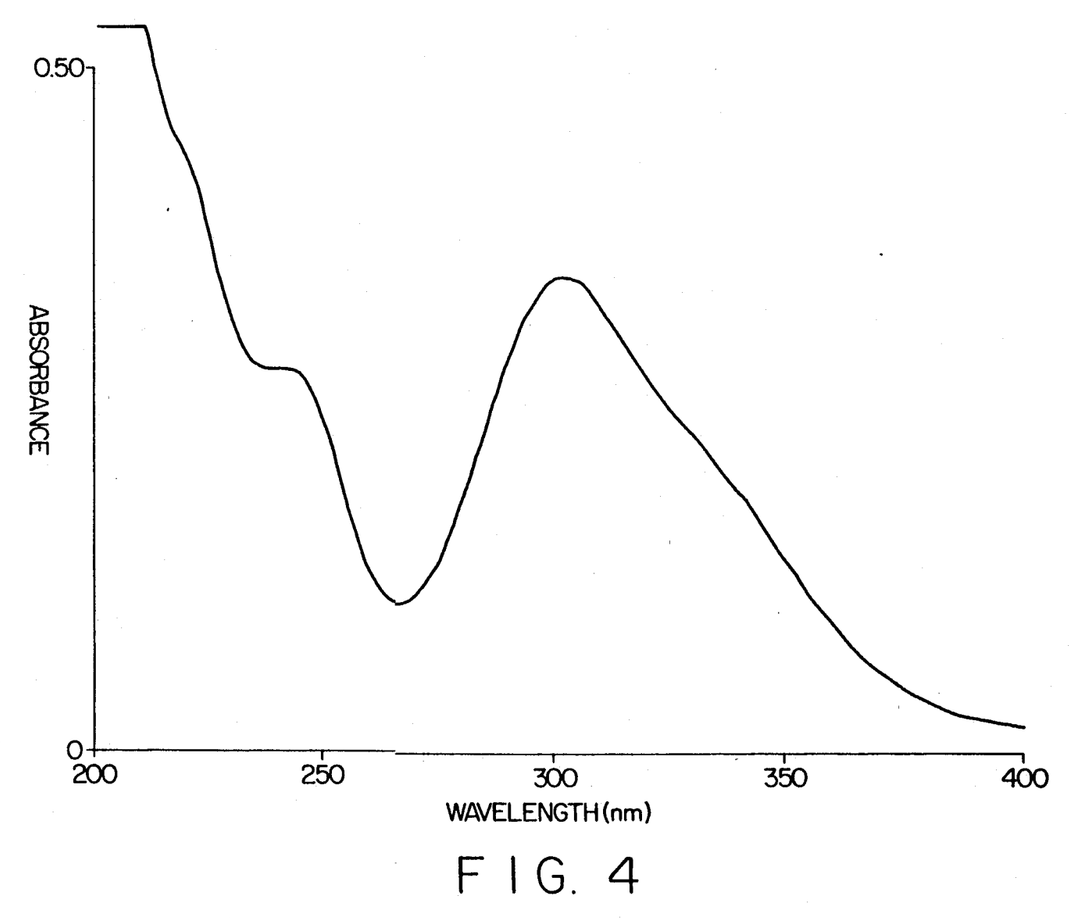
FIG. 4 shows the ultraviolet absorption spectrum of the organosilicon compound of this invention obtained in Example 2.

The infrared and ultraviolet spectra of the product (solute concentration 1.28 mg/100 ml ethanol) are shown in FIG. 3 and FIG. 4 respectively, and its solubility in various silicone oils is shown in Table 1.

From the above results, it is seen that although the benzophenone type compound used as starting material itself has poor solubility in silicone oils, the organosilicon compound obtained by this invention has a very high solubility. In addition, it strongly absorbs ultraviolet light. We shall now give some examples of cosmetic preparations obtained by blending the organosilicon compounds obtained in the above examples.

PREPARATION 1

| Oil-Based Foundation | |
| --- | --- |
| Component (A): | |
| Kaolin: | 20.0 wt % |
| Titanium oxide: | 12.0 wt % |
| Sericite: | 8.0 wt % |
| Coloring pigment | suitable quantity |
| Component (B): | |
| Carnauba wax: | 4.0 wt % |
| Dimethylpolysiloxane: (viscosity at 25° C.: 50 cs) | 5.0 wt % |
| Organosilicon compound obtained in Example 1: | 8.0 wt % |
| Octamethylcyclotetrasiloxane: | 42.0 wt % |
| Sorbitan sesquioleate: | 1.0 wt % |
| Component (C): | |

-continued

| Oil-Based Foundation | |
| --- | --- |
| Perfume | suitable quantity |

After stirring component (B) at 70° C. and dissolving the constituents to obtain a homogeneous solution, Component (A) was added and stirred to disperse it, and the product cooled. The resulting mixture was kneaded 3 times in a 3 roller roll mill, and component (C) was added so as to obtain an oil-based foundation. This oil-based foundation had excellent ultraviolet absorption, water resistance and extensibility, and was pleasant to use.

PREPARATION 2

| Solid Foundation | |
| --- | --- |
| Component (A): | |
| Titanium oxide: | 20.0 wt % |
| Mica: | 36.0 wt % |
| Sericite: | 10.0 wt % |
| Talc: | 10.0 wt % |
| Coloring pigment | suitable quantity |
| Component (B): | |
| Dimethylpolysiloxane: (viscosity at 25° C.: 50 cs) | 12.5 wt % |
| Organosilicon compound obtained in Example 2: | 10.0 wt % |
| Lipophilic glycerine monooleate: | 1.5 wt % |
| Methyl paraoxybenzoate | suitable quantity |
| Perfume | suitable quantity |

After pulverizing Component (A) in a 2 roller roll mill and adding Component (B) in the form of a homogeneous solution, the product was stirred and mixed. The resulting mixture was kneaded 3 times in a 3 roller roll mill, and a solid foundation was obtained.

This solid foundation had excellent ultraviolet absorption and water resistance, and was pleasant to use.

PREPARATION 3

| Anti-Sunburn Cream | |
| --- | --- |
| Component (A): | |
| Octamethylcyclotetrasiloxane: | 40.0 wt % |
| Organosilicon compound obtained in Example: 1: | 20.0 wt % |
| Trimethylsiloxypolysilioate: | 25.0 wt % |
| Liquid paraffin: | 10.0 wt % |
| Carnauba wax: | 5.0 wt %% |
| Component (B): | |
| Perfume | suitable quantity |

Component (A) was stirred at 80° C. After forming a homogeneous solution and cooling, Component (B) was added, and an anti-sunburn cream was thus obtained. This anti-sunburn cream had excellent ultraviolet absorption and water resistance, and was pleasant to use.

PREPARATION 4

| Anti-Sunburn Milk | |
| --- | --- |
| Component (A): | |
| Decamethylcycloheptasiloxane: | 7.0 wt % |
| Organosilicon compound obtained in Example 2: | 3.0 wt % |
| Dimethylpolysiloxane: (viscosity at 25° C.: 350 cs) | 2.0 wt % |
| Stearic acid: | 2.0 wt % |

| Anti-Sunburn Milk | |
| --- | --- |
| Self-emulsifying glycerine monostearate: | 1.0 wt % |
| Cetanol: | 1.0 wt % |
| Component (B); | |
| Purified water: | 72.5 wt % |
| Triethanolamine: | 1.0 wt % |
| Propylene glycol: | 3.0 wt % |
| Titanium oxide: | 5.0 wt % |
| Bentonite: | 0.5 wt % |
| Methyl paraoxybenzoate: | suitable quantity |
| Componet (C); | |
| Perfume: | suitable quantity |

Component (A) was stirred at 80° C. Component (B) was then stirred at 80° C., and the resulting homogeneous dispersion was added gradually to Component (A) with stirring.

After cooling, Component (C) was added and mixed to obtain an anti-sunburn milk.

This anti-sunburn milk was pleasant to use.

PREPARATION 5

| Hair Cream | |
| --- | --- |
| Component (A); | |
| Methylphenylpolysiloxane: | 17.0 wt % |
| (viscosity at 25° C.: 20 cs) | |
| Organosilicon compound obtained in Example 1: | 3.0 wt % |
| Camellia oil: | 10.0 wt % |
| Bleached beeswax: | 5.0 wt % |
| Self-emulsifying glycerine monostearate: | 3.0 wt % |
| Polyoxyethylenesorbitan monostearate: | 3.0 wt % |
| (20 EO) | |
| Reduced lanolin: | 1.5 wt % |
| Microcrystalline wax: | 2.0 wt % |
| Methyl paraoxybenzoate: | suitable quantity |
| Component (B); | |
| Purified water: | 51.0 wt % |
| Boron sand: | 0.5 wt % |
| Glycerine: | 3.0 wt % |
| Carboxyvinyl polymer: | 0.2 wt % |
| Component (C); | |
| Perfume: | 0.8 wt % |

Component (A) was stirred at 80° C. Component (B), which had been heated to 80° C. to dissolve it, was then added to Component (A) with further stirring, and the mixture cooled to 60° C. After adding Component (C) to the resulting solution, the mixture was cooled to 30° C. to obtain a hair cream. This hair cream had excellent ultraviolet absorption, and was pleasant to use.

PREPARATION 6

| Stick Lipstick | |
| --- | --- |
| Component (A); | |
| Methylphenylpolysiloxane: | 46.5 wt % |
| (viscosity at 25° C.: 20 cs) | |
| Organosilicon compound obtained in Example 2: | 10.0 wt % |
| Reduced lanolin: | 20.0 wt % |
| Carnauba wax: | 4.5 wt % |
| Candelira wax: | 9.0 wt % |
| Ceresin wax: | 2.5 wt % |
| Bleached beeswax: | 1.5 wt % |
| Cacao butter: | 4.0 wt % |
| Saccharose fatty acid ester: | 2.0 wt % |
| Antioxidant: | suitable quantity |
| Component (B); | |
| Allantoin: | suitable quantity |

| Stick Lipstick | |
| --- | --- |
| No. 3 red aluminium lake: | suitable quantity |
| Component (C); | |
| Perfume: | suitable quantity |

After stirring and dissolving Component (A) at 85° C. part was removed, Component (B) was added, and the mixture kneaded 3 times in a 3 roller roll mill to obtain a colored paste.

This color paste was then added to the remainder of component (A), and mixed by a Disper Mixer to give a uniform dispersion. Component (C) was then added, the mixture cast in a mold, and cooled rapidly to obtain a stick lipstick. This lipstick had excellent ultraviolet absorption and water resistance, a lustrous sheen, and was pleasant to use.

PREPARATION 7

| Eye-Shadow | |
| --- | --- |
| Component (A); | |
| Pearl essence | 10.0 wt % |
| Ultramarine blue | 5.0 wt % |
| Component (B); | |
| Dimethylpolysiloxane | 28.0 wt % |
| (viscosity at 25° C.: 20 cs) | |
| Octamethylcyclotetrasiloxane | 42.0 wt % |
| Organosilicon compound obtained in Example 1: | 5.0 wt % |
| Reduced lanolin | 5.0 wt % |
| Microcrystalline wax | 5.0 wt % |
| Component (C); | |
| Perfume | suitable quantity |

Component (B) was stirred and dissolved at 80° C. then Component (A) was added and dispersed with stirring. After allowing to cool, Component (C) was added, and the resulting mixture was kneaded 3 times in a 3 roller roll mill to obtain an eye shadow in the form of a cream. This eye shadow had excellent ultraviolet absorption and water resistance, and was pleasant to use.

PREPARATION 8

| Mascara | |
| --- | --- |
| Component (A); | |
| Isoparaffin: | 20.0 wt % |
| Octamethylcyclotetrasiloxane: | 20.0 wt % |
| Organosilicon compound obtained in Example 2: | 7.0 wt % |
| Aluminium stearate: | 1.0 wt % |
| Component (B); | |
| Bentonite: | 15.0 wt % |
| Methylphenylpolysiloxane: | 7.0 wt % |
| (viscosity at 25° C.: 20 cs) | |
| Candelira wax: | 10.0 wt % |
| Hydrogenated polybutene: | 5.0 wt % |
| Methyl paraoxybenzoate: | suitable quantity |
| Component (C); | |
| Kaolin: | 5.0 wt % |
| Black iron oxide: | 5.0 wt % |

Component (A) was stirred at 80° C. to form a gel-like solution, Component (B) which had been stirred at 80° C. until homogeneous was added to give a uniform dispersion, and after cooling, Component (C) was added. The resulting mixture was then kneaded 3 times in a 3 roller roll mill to obtain a mascara. This mascara had excellent ultraviolet absorption and water resistance, and it was pleasant to use.

The above results show that the organosilicon compound of this invention is highly superior as a compounding agent in cosmetics.

What is claimed is:

1. An organosilicon compound having a benzophenone skeleton represented by the formula wherein

"n" is an integer in the range of 0–100, $R^1$ are similar or dissimilar saturated hydrocarbon groups with a number of carbon atoms in the range of 1–30 or a phenyl group, $R^2$ is a monovalent organic group represented by the formula $-(CR^3{}_2CR^3(H)\ CR^3{}_2)-R^4$, $R^3$ is a hydrogen atom or a saturated monovalent hydrocarbon group with 1–5 carbon atoms, and $R^4$ is a group represented by the formula:

or wherein $R^5$ is a hydrogen atom or hydroxyl group, $R^6$ are hydrogen atoms or similar or dissimilar monovalent saturated or unsaturated groups with 1–10 carbon atoms, "a" is an integer in the range of 0–3, and "b" is an integer in the range of 0–4.

2. The organosilicon compound of claim 1, wherein "n" is an integer of 0–10.

* * * * *